United States Patent [19]

Laghi

[11] Patent Number: 5,507,834

[45] Date of Patent: Apr. 16, 1996

[54] TRANSPARENT SILICONE SUCTION SOCKET

[76] Inventor: Aldo A. Laghi, 13 Meridian La., Ballston Lake, N.Y. 12065

[21] Appl. No.: 245,096

[22] Filed: May 17, 1994

[51] Int. Cl.⁶ .......................................... A61F 2/80
[52] U.S. Cl. .................................. 623/36; 623/34
[58] Field of Search .......................... 623/32–37

[56] References Cited

U.S. PATENT DOCUMENTS

| 3,957,713 | 5/1976 | Jeram et al. | 524/703 |
|---|---|---|---|
| 4,300,245 | 11/1981 | Saunders | 623/35 |
| 4,413,359 | 11/1983 | Akiyama et al. | 623/36 X |
| 4,923,474 | 1/1990 | Klasson et al. | 623/33 |
| 5,007,937 | 4/1991 | Fishman et al. | 623/34 |
| 5,246,464 | 9/1993 | Sabolich | 623/33 |
| 5,314,497 | 5/1994 | Fay et al. | 623/34 |
| 5,376,131 | 12/1994 | Lenze et al. | 623/34 |

FOREIGN PATENT DOCUMENTS 0031750  3/1978  Japan .......................... 623/33

*Primary Examiner*—David H. Willse
*Attorney, Agent, or Firm*—Joseph C. Mason, Jr.; Ronald E. Smith

[57] ABSTRACT

A clear liquid silicone rubber is modified by the addition of an elongation enhancer. The resulting silicone compound is molded into a form that overlies the residual limb of an amputee and provides an interface member between the residual limb and a prosthesis. A nonsilicone substrate is partially embedded in the bottom of the interface member and a nonembedded part of the substrate provides a connection to the prosthesis. Electrons are stripped from the surface of the substrate, an adhesion promoter is applied, and the clear silicone polymer is vulcanized onto the substrate so that it bonds to the silicone portion of the adhesion promoter.

1 Claim, 2 Drawing Sheets

TRANSPARENT SILICONE SUCTION SOCKET

BACKGROUND OF THE INVENTION

1. Field of the invention

This invention relates, generally, to an interface member worn upon the residual limb of an amputee to provide a cushion between the residual limb and a prosthesis. More particularly, it relates to a transparent silicone interface.

2. Description of the prior art

Prosthesis sockets are hard, rigid devices that receive the residual limb, also known as the stump, of an amputee. Individuals requiring the use of such sockets typically wear several layers of socks over their residual limbs in an effort to provide a cushioning means between the stump and the socket; the socks work reasonably well as a cushioning means but do not serve the function of holding the socket onto the residual limb.

Accordingly, several inventors have developed means for cushioning the residual limb and holding the socket onto the limb. For example, U.S. Pat. No. 4,923,475 to Gosthnian et. al. discloses a stump-receiving socket having a plurality of inflatable bladders, each of which includes a relatively soft, flexible membrane made of a suitable material such as polyurethane. The idea behind the design is to maximize the weight-bearing area while minimizing or eliminating pressure points through the judicious use of the inflatable bladders.

The materials used to provide the cushioning means tend to exhibit poor anti-tear properties. Thus, U.S. Pat. No. 4,923,474 to Klasson et. al. discloses a cushioning member made of an elastomeric material having a fiber embedded therein to increase its strength.

Although some of the earlier interface members have a shape and thickness similar to that of the present invention, they are opaque and thus pose problems to the prosthetist when fitting the interface member to a patient. Most of the earlier interface members also lack strength and durability. The earlier members that do have adequate strength and durability are expensive to manufacture because they rely upon fabric embedded within the material of which they are made to supply the needed strength.

Moreover, the attachment of the interface members of the prior art to sockets has proven problematic. The conventional device employed to secure the interface member to the socket is typically bonded to the lowermost end of the interface member; it is releasably connected to the socket. The device is formed of a nonsilicone material, however, and suitable bonding techniques for bonding such a device to a silicone interface member have not been found.

What is required, then, is a transparent silicone socket interface member having strength and durability derived from its formulation and not from fabrics embedded therein. A need also exists for a new method of securing a connector device to the lowermost end of a socket interface member. A transparent, fabric-free socket interface member having enhanced strength and durability would enable the prosthetist to observe socket pressures and tensions, especially in high load areas. Scar tissue, skin grafts, and invaginated areas could be easily monitored to ensure total contact, and silicone putty could be applied where needed to eliminate voids. The position of the interface member and all putty applications could be checked for proper positioning during and after socket application.

However, in view of the state of the art at the time the present invention was made, it was not obvious to those of ordinary skill in this art how such a silicone suction socket could be provided, nor was it obvious that a clear silicone suction socket should be provided.

SUMMARY OF THE INVENTION

The socket liner or interface member of this invention is made of clear, fabric-free silicone having high elongation. It allows the prosthetist to see if there are any skin folds or air bubbles when the liner is fitted onto the residual limb. A connector has an upper part embedded within the lowermost end of the liner and an exposed lower part of the connector releasably connects the liner to the socket.

Due to the shape of the liner, a silicone having high viscosity cannot be employed because high viscosity silicone will not properly fill a mold.

However, low viscosity silicone tends to lack high tear strength; for this reason, the art has taught the use of fabric embedded within a low viscosity silicone.

If it is desired to increase the strength of the silicone without employing an embedded fabric, the desire is frustrated because strength is normally increased by introducing higher levels of reinforcing filler; such increase in reinforcing filler, however, substantially increases the viscosity of the silicone, and, again, high viscosity silicone will not properly fill a mold. Thus, a different method must be found for increasing the tear strength of the liner without substantially increasing its viscosity. The present invention provides such a method.

A commercially available silicone-based compound of the silicone rubber type is purchased.

An elongation enhancer is added to this compound.

The elongation enhancer is a polydimethyl siloxane polymer methyl terminated, free of hydroxyl groups, and of low viscosity. Alternatively, it may be a polydimethyl siloxane, vinyl terminated of high viscosity, or a cyclo siloxane with 4 or 5 silicone atoms.

The insert at the closed end of the liner that attaches the liner to the socket is a nonsilicone member, as aforesaid. The bonding of silicone to a nonsilicone substrate is somewhat problematic; this invention includes a novel method for accomplishing the bonding. More particularly, electrons are first removed from the surface of the substrate (the insert at the closed end of the liner); the removal is accomplished by applying strong oxidizing or reducing agents such as acids, by subjecting the substrate to the corona effect, by application of an oxidizing flame, or by plasma ionization. In all respects, the electron removal is a temporary effect. Removal of the electrons temporarily positively charges the surface of the substrate; before the effect wears off, i.e., before the surface becomes electrically neutral again, a commercially available organo-functional silane primer is applied under controlled conditions as an adhesion promoter. The organic portion of the primer bonds the substrate, and the silane portion of the adhesion promoter is then hydrolized to silicone. The insert is placed in the mold and then the silicone compound is injected into the mold and vulcanized at elevated temperature. This forms the silicone compound into the desired shape and bonds it to the insert.

The result is a puncture and tear-resistant clear silicone that has been proven effective as a limb-socket interface. The flexibility of the interface helps to improve circulation and substantially eliminates noticeable shear and friction forces against the skin.

Importantly, the embedding of the insert into the bottom of the interface ensures that the insert and interface will not separate from one another.

It is therefore understood that an important object of this invention is to provide a comfortable limb-socket interface.

Another important object is to provide such an interface in transparent or translucent form so that the prosthetist can observe socket pressures and tensions, especially in high load areas, and can assure the avoidance of air entrapment.

These and other important objects, features and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
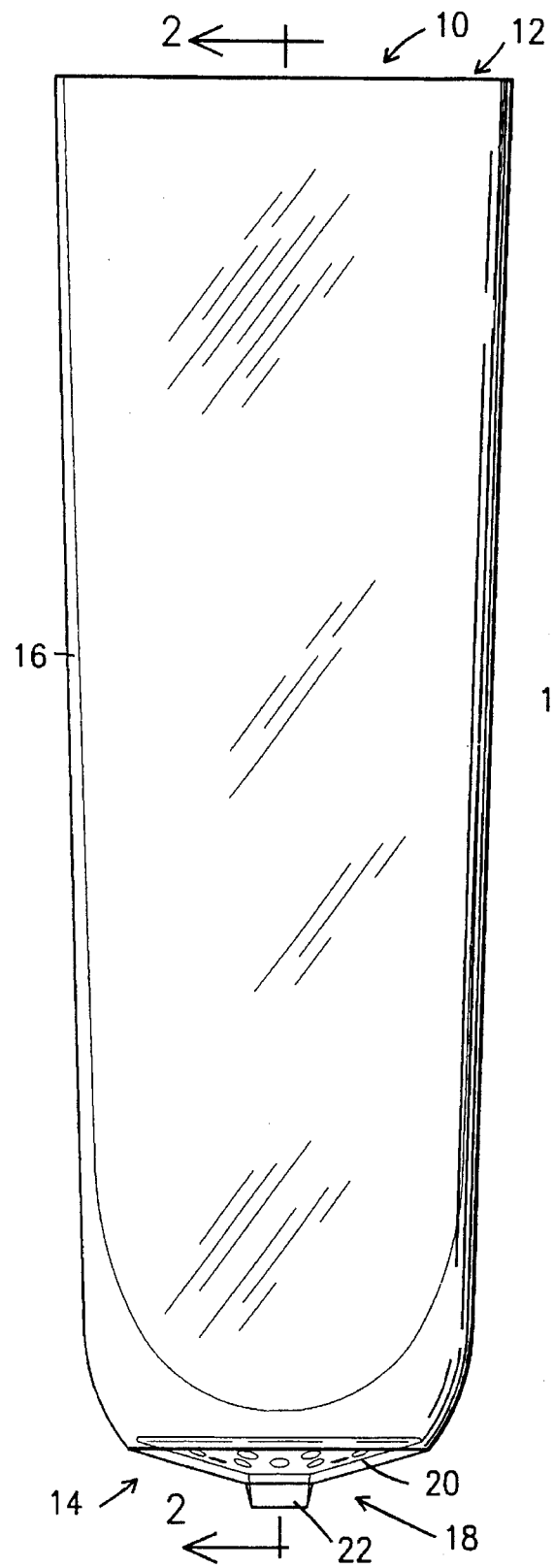
FIG. 1 is a front elevational view of the novel socket-limb interface.
Figure 2:
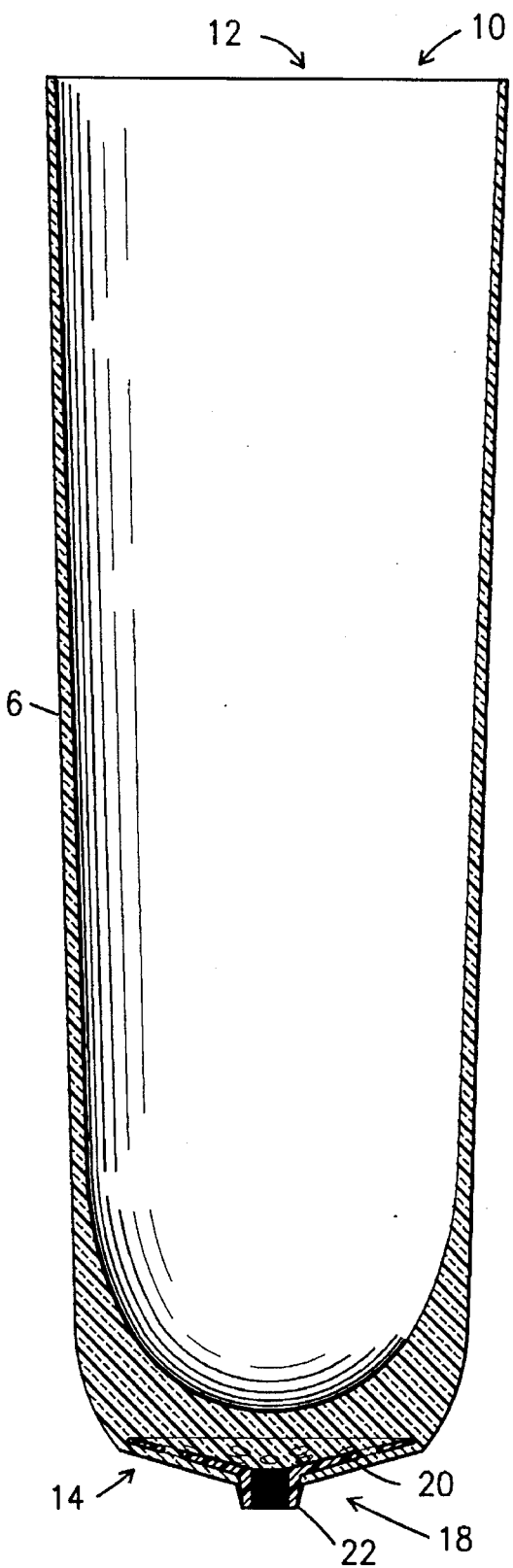
FIG. 2 is a longitudinal sectional view thereof.

Referring now to FIGS. 1 and 2, it will there be seen that the novel limb-socket interface of this invention is denoted by the reference numeral 10 as a whole. Many sizes are produced to fit most patients, having a circumference measured at six centimeters above the distal end from ten for upper extremities of children to sixty for above knee amputees of large size.

Interface 10 has an open upper end 12 for receiving a residual limb, not shown, a closed bottom end 14, and sidewalls 16 of predetermined thickness. The preferred thickness of the sidewalls is about 1.5 mm. Note that the thickness is greater at the bottom end than in the sidewalls; the preferred thickness of the silicone at said bottom end is about 12.0 mm.

Figure 3:
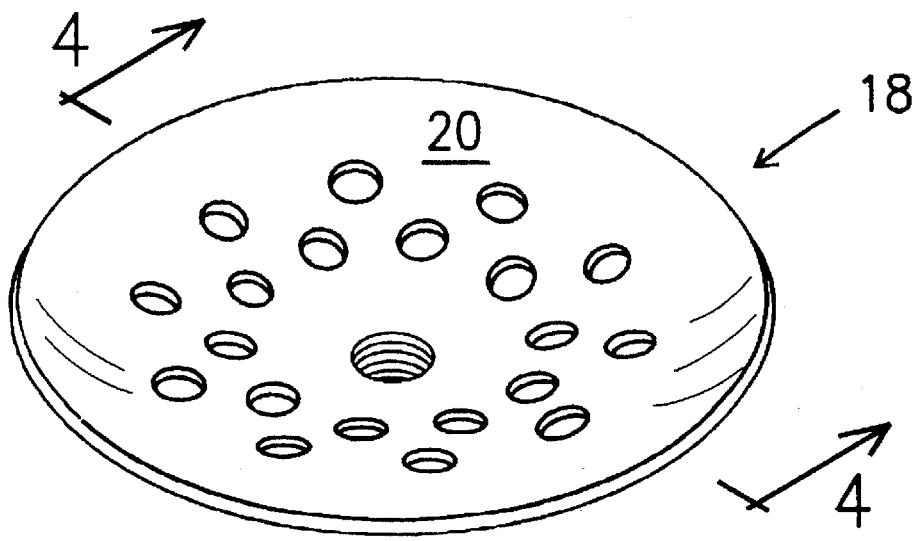
FIG. 3 is a perspective view of the nonsilicone insert.
Figure 4:
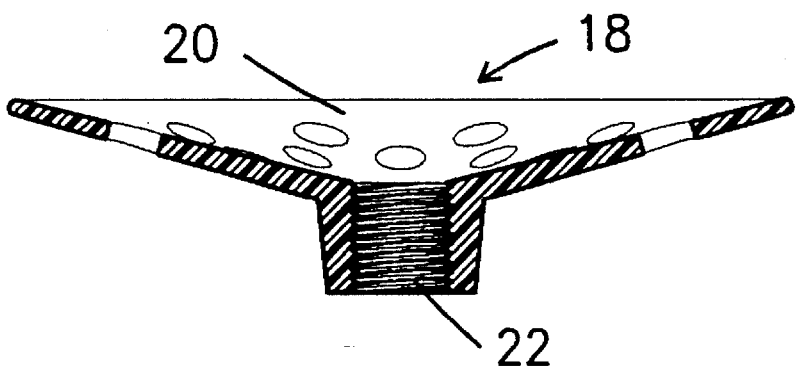
FIG. 4 is a sectional view taken along line 4—4 in FIG. 3.

A nonsilicone insert member 18, also shown in FIGS. 1 and 2 but best seen in FIGS. 3 and 4, is partially embedded within the thickened silicone at the bottom end of the interface as shown in the first two Figures. More particularly, base 20 of insert member 18 is embedded within said thickened silicone, and internally threaded boss part 22 thereof is screw threadedly engageable to an externally threaded screw (not shown) that projects upwardly from the socket to prevent unwanted separation of the socket and interface.

As mentioned above, low viscosity silicone tends to lack high tear strength but the introduction of reinforcing filler to increase the tear strength substantially increases the viscosity of the silicone. Thus, to increase the tear strength of the interface without substantially increasing its viscosity, a commercially available silicone compound A & B is purchased.

This compound can be of two types commonly referred to as

1. Addition cure, platinum catalyst
2. Condensation cure, tin catalyst

Each of these two types are disclosed in more detail as follows:

1. Addition cure, Platinum catalyst. This is the preferred type: it consists of two components, A & B, which in turn consist of the following:

Component A: A polydimethylsiloxane polymer that is vinyl terminated. The viscosity of this polymer strictly correlates with its molecular weight and, as a consequence, with its vinyl activity. The viscosity of this polymer is as follows:

| typical | 50,000 cps |
| preferred | 20,000 to 60,000 cps |
| adequate | 5,000 to 100,000 cps |

The concentration of this element of component A is established at 100 parts as a reference.

The compound further includes a silica filler which can be of either of the following types:

Fumed silica, which is called such because it is produced by the combustion of a silane, typically trichlorosilane; this is the preferred type.

Precipitated silica, called such because it is produced by precipitation from an aqueous solution.

In either case, the silica must be treated to neutralize the electronically active sites present on its surface. If such sites are not neutralized, the interaction between the electronic orbitals of the polydimethysilicone polymer and the active sites of the silica is such that the compound will become so viscous as to be unprocessable.

The treatment of the filler is effected by using a silane or a cyclic siloxane polymer; the preferred treating agents are hexamethyldisilazane and octyl methyl tetra siloxane.

The concentration of the filler is as follows:

| typical | 25 parts |
| preferred | 15 to 35 parts |
| adequate | 10 to 40 parts |

The platinum catalyst is cycloplatinic acid in a solution of octyl alcohol.

The concentration of active platinum is as follows:

| typical | 15 ppm |
| preferred | 10 to 30 ppm |
| adequate | 5 to 50 ppm |

Component B: A polydimethylsiloxane polymer vinyl terminated identical to the one in Component A.

Concentration: 100 parts (reference)

Component B further includes a polydimethylsiloxane polymer with hydrogen on the chain, commonly called methyl hydrogen, which acts as a crosslinker.

| Viscosity: | |
| --- | --- |
| typical | 40 cps |
| preferred | 20 to 5,000 cps |
| adequate | 10 to 3,000 cps |

The typical hydrogen concentration is the following: moles of SiH per mmoles of vinyl in the "B" component

| | |
|---|---|
| typical | 5.0:1 |
| preferred | 4.0:1 to 6.0:1 |
| adequate | 3.0:1 to 10.0:1 |

The Inhibitor of Compound B is acetylenic alcohol or tertiary isobutyl alcohol.

| Concentration: | |
|---|---|
| typical | 2,000 ppm |
| preferred | 1,000 to 5,000 ppm |
| adequate | 0 to 10,000 ppm |

Components A & B are intended to be mixed in a 1:1 ratio. The typical property profile of this silicone compound once vulcanized indicates its suitability to produce comfortable and strong suction sockets.

| | typical | preferred | adequate |
|---|---|---|---|
| Durometer (shore A) | 10 | 7 to 12 | 5 to 18 |
| Tensile (psi) | 700 | 650 to 800 | 600 to 900 |
| Elongation (%) | 950 | 900 to 1200 | 800 to 1200 |
| Tear (ppi) | 95 | greater than 85 | greater than 80 |

A silicone oil, as elongation enhancer, is added to the purchased compound at the time components A & B are mixed together.

Components A & B and the silicone oil are all mixed at the same time in an automatic mixing and dispensing machine and mixed through a static mixer. An alternative method employs a batch mixer and includes the step of evacuating the mixture to remove the entrapped air.

The elongation enhancer consists of either of the following:

Polydimethylsiloxane methyl terminated polymer (preferred type). Its viscosity is as follows:

| | |
|---|---|
| typical | 100 cps |
| preferred | 10 to 500 |
| adequate | 5 to 20,000 |

Cyclic siloxane such as octyl methyl tetra siloxane or decamethylpentasiloxane.

Polydimethylsiloxane vinyl terminated having the following viscosity:

| | |
|---|---|
| typical | 165,000 cps |
| preferred | 65,000 to 180,000 |
| adequate | 10,000 to 200,000 |

The concentration of either to be used for 100 parts of Components A and B is as follows:

| | |
|---|---|
| typical | 23 |
| preferred | 20 to 30 |
| adequate | 15 to 35 |

The silicone oil modifies the elongation characteristics of the vulcanized compound; specifically, the modulus is reduced. This results in a more comfortable socket for the amputee.

| Final Properties | | | |
|---|---|---|---|
| | typical | preferred | adequate |
| Durometer (shore A) | 4 | 2 to 7 | 1 to 12 |
| Tensile (psi) | 650 | 600 to 800 | 500 to 800 |
| Elongation (%) | 1100 | 1000 to 1400 | 950 to 1300 |
| Tear (ppi) | 80 | greater than 75 | greater than 70 |

The insert is placed in the mold and the silicone is injected and vulcanized at elevated temperature.

Molding Parameters
1. Addition Cure Platinum Catalyst

| | typical | preferred | adequate |
|---|---|---|---|
| Injection Pressure (psi) | 3000 | 2000–4000 | 1000–6000 |
| Injection Speed (grams-min) | 400 | 200–600 | 100–800 |
| Mold Temperature (F.) | 280 | 230–350 | 200–400 |
| Curing Time (minutes) | 3 | 2–5 | 1–10 |

2. Condensation Cure, Tin Catalyst

A silicone base is purchased that consists of the following:
A polydimethylsiloxane polymer hydroxyl terminated of the following viscosity:

| | |
|---|---|
| typical | 30,000 cps |
| preferred | 20,000 to 50,000 |
| adequate | 10,000 to 80,000 |

Concentration of the polydimethylsiloxane polymer is established at 100 parts as a reference.

This alternative compound includes silica filler identical in composition and concentration as described in connection with the preferred (addition cure, platinum catalyst) type of compound.

It further includes a crosslinking agent such as tetraorthosilicate or a partially hydrolizated silicate. These are commonly used and widely available commercially. The concentration of the crosslinking agent is as follows:

| | |
|---|---|
| typical | 3 parts |
| preferred | 2 to 4 parts |
| adequate | 1.5 to 6 parts |

A polydimethylsiloxane methyl terminated polymer is used as an elongation enhancer. This is identical to the elongation enhancer used in the preferred type of compound. The concentration used is as follows:

| | |
|---|---|
| typical | 23 parts |
| preferred | 20 to 30 parts |
| adequate | 15 to 35 parts |

A commercially available stannous tin octoate or dibutyl tin laureate is also employed, the concentration of which is as follows:

| | |
|---|---|
| typical | 0.5 parts |
| preferred | 0.1 to 1 parts |
| adequate | 0.05 t 3 parts |

The ingredients are mixed in a batch mixer or in a continuous mixer and evacuated to remove the air entrapped during mixing.

The compound is then injected into the mold and then vulcanized at room temperature or slightly thereabove.

Molding Parameters

| Injection Pressure | 600 | 300–1000 | 0*–2000 |
| --- | --- | --- | --- |
| Injection Speed (grams/minute) | 200 | 100–500 | 50–800 |
| Mold Temperature (F.) | 80 | 60–140 | 50–190 |
| Curing Time (hrs) | 0.3 | 0.2–2.0 | 0.2–8 |

*0 Injection Pressure = Atmospheric Casting

Materials having an elongation of less than eight hundred per cent are within the scope of this invention, but most patients report that such materials produce a feel of being excessively tight. Similarly, materials having less than seventy-five ppi tear are within the scope of this invention but they rip easily in service and they are difficult to remove from the mold without tearing. (The high temperatures of a mold greatly reduce tear strength). Materials having a tensile strength higher than nine hundred psi are also within the scope of this invention, but produce a feel considered too tight by most patients. Materials having a tensile strength below six hundred psi were not tested because their elongation and tear properties would be unacceptable. Finally, materials softer than seven Shore A typically had tear strengths below seventy five pounds per inch and ripped when being removed from hot molds.

This invention is clearly new and useful. Moreover, it was not obvious to those of ordinary skill in this art at the time it was made, in view of the prior art considered as a whole as required by law.

It will thus be seen that the objects set forth above, and those made apparent from the foregoing description, are efficiently attained and since certain changes may be made in the above construction without departing from the scope of the invention, it is intended that all matters contained in the foregoing construction or shown in the accompanying drawings shall be interpreted as illustrative and not in a limiting sense.

It is also understood that the following claims are intended to cover all of the generic and specific features of the invention herein described, and all statements of the scope of the invention which as a matter of language, might be said to fall therebetween.

Now that the invention has been described,

What is claimed is:

1. An apparatus adapted to be worn on a residual limb to serve as an interface between the residual limb and a prosthesis, comprising:

a base material shaped to fit within said prosthesis and having a thickened distal free end;

said base material being a clear liquid silicone rubber;

said liquid silicone rubber having a Shore A hardness substantially between seven and twenty;

said liquid silicone rubber having a tensile strength substantially between six hundred and nine hundred pounds per square inch;

said liquid silicone rubber having an ultimate elongation greater than about eight hundred per cent;

said liquid silicone rubber having a tear strength greater than about seventy-five pounds per inch;

an elongation enhancer compounded with said liquid silicone rubber;

said liquid silicone rubber being transparent;

a nonsilicone insert member partially embedded within said thickened distal free end, said nonsilicone insert member being adapted to releasably engage said prosthesis;

whereby said apparatus is soft, durable, non-toxic, non-allergenic and exhibits high elongation.

* * * * *